US00PP24815P3

(12) United States Plant Patent
Olesen et al.

(10) Patent No.: US PP24,815 P3
(45) Date of Patent: Aug. 26, 2014

(54) ***CLEMATIS* PLANT NAMED 'EVIPO045'**

(50) Latin Name: *Clematis cartmanii*
Varietal Denomination: Evipo045

(75) Inventors: Mogens Nyegaard Olesen, Fredensborg (DK); Raymond J. Evison, St. Sampsons (GB)

(73) Assignee: Poulsen Roser A/S, Fredensborg (DK)

( * ) Notice: Subject to any disclaimer, the term of this patent is extended or adjusted under 35 U.S.C. 154(b) by 0 days.

(21) Appl. No.: 13/507,015

(22) Filed: May 31, 2012

(65) Prior Publication Data

US 2013/0326776 P1 Dec. 5, 2013

(51) Int. Cl.
*A01H 5/00* (2006.01)

(52) U.S. Cl.
USPC ..... Plt./228

(58) Field of Classification Search
USPC ..... Plt./228
See application file for complete search history.

*Primary Examiner* — Kent L Bell

(57) ABSTRACT

A new *Clematis* plant with a compact growth habit, profuse, white flowers, and continuous summer flowering. The variety successfully propagates from softwood cuttings and is suitable for cultivation in commercial nursery culture. This new and distinct variety has shown to be uniform and stable in the resulting generations from asexual propagation from vegetative cuttings.

2 Drawing Sheets

Botanical classification: Genus: *Clematis*. Species: *cartmanii*.
Variety denomination: 'Evipo045'.

SUMMARY OF THE CLAIMED PLANT

The present invention constitutes a new and distinct variety of *Clematis* plant which originated from a controlled crossing between the female seed parent, an un-named seedling, and the male pollen parent, an un-named seedling The two parents were crossed during the summer of 1995 and the resulting seeds were planted the following winter in a controlled environment in Guernsey, Channel Islands United Kingdom. The new variety named 'Evipo045' originated as a single seedling from the stated cross.

The new *Clematis* plant may be distinguished from its female seed parent and male pollen parent primarily by flower size and compactness of growh habit.

The objective of the hybridization of this *Clematis* plant was to create a new and distinct variety for nursery culture with unique qualities such as:

1. Uniform and abundant white flowers;
2. Vigorous and compact growth, making the variety suitable for container culture; and
3. Early flowering.

This combination of qualities was lacking in *Clematis* plants that were in commercial cultivation and the qualities have been substantially achieved in the new variety.

'Evipo045' was selected by Mogens N. Olesen and Raymond J. Evison in their *Clematis* development program in the Channel Islands, United Kingdom in 1996. Asexual reproduction of 'Evipo045' by means of vegetative cuttings and traditional layering was first performed by Mogens N. Olesen and Raymond J. Evison in the nursery during the summer of 1996. This initial and subsequent asexual propagations have demonstrated that the characteristics of 'Evipo045' are true to type and are transmitted from one generation to the next.

BRIEF DESCRIPTION OF THE DRAWING

The accompanying color illustrations show as true as is reasonably possible to obtain in color photographs of this type the typical characteristics of the buds, flowers, leaves, and stems, of 'Evipo045'. Specifically illustrated in FIG. 1 of the drawings are flowers detached, flower pedicels, leaves and stems.

DETAILED DESCRIPTION OF THE VARIETY

Figure 1:
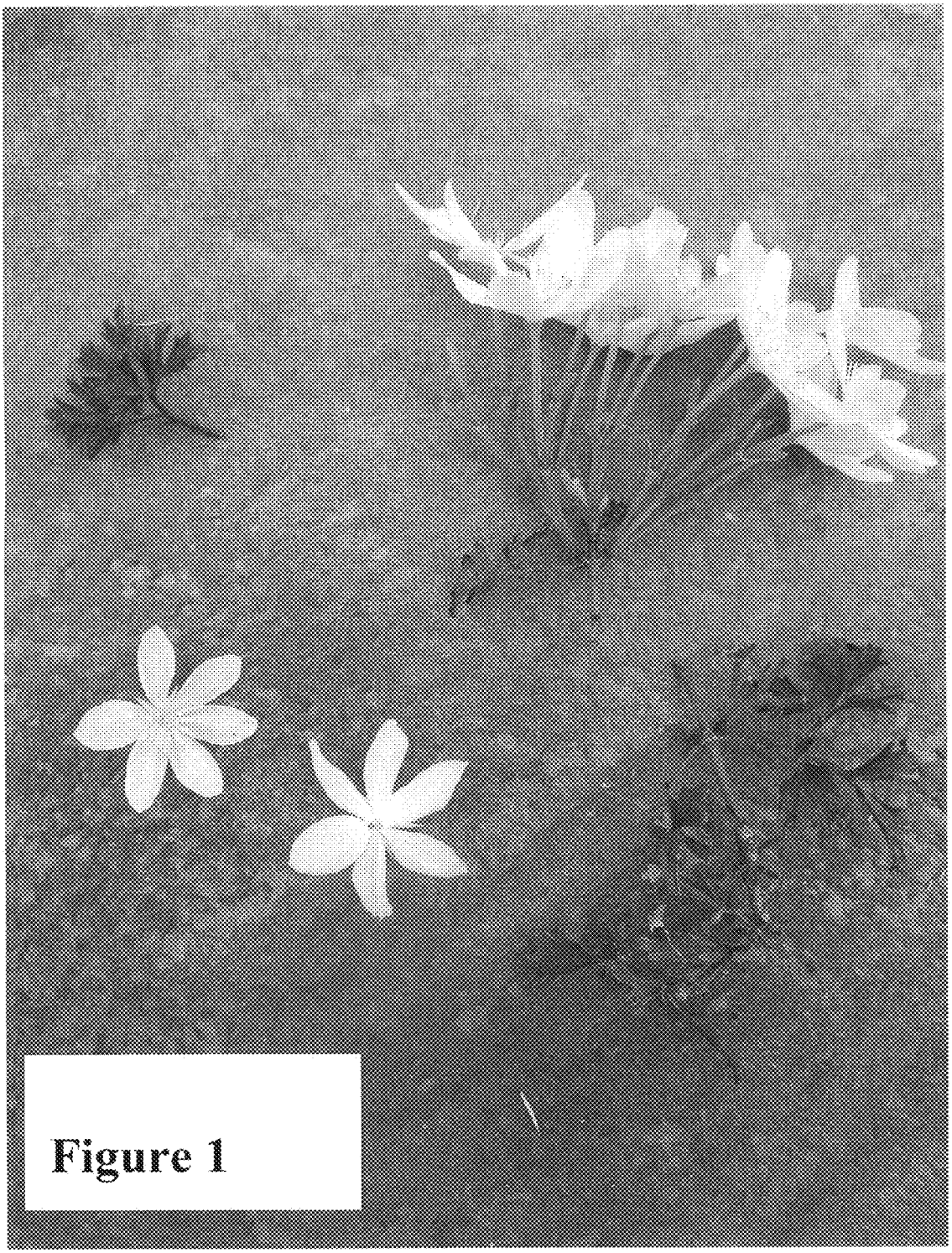
Figure 2:
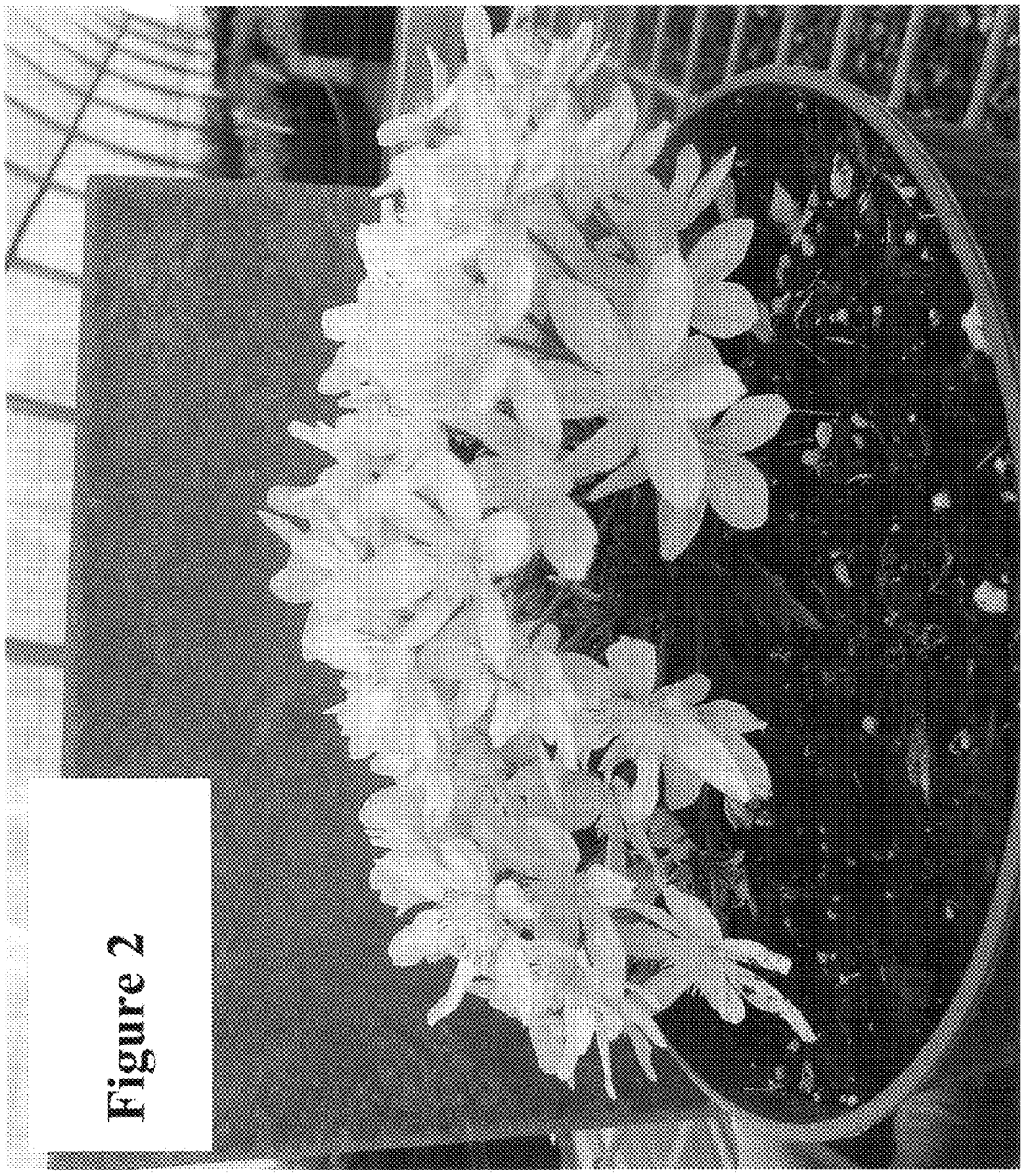
FIG. 2 shows open flowers on the plant.

The following is a detailed description of 'Evipo045', as observed in its growth throughout in a glasshouse located in Lancaster, Pa. Observed plants were cultivated for a period of 18 months in 2 liter containers. Certain phenotypical characteristics of the variety may vary under different environmental, cultural, agronomic, seasonal, and climatic conditions. Color references are made using The Royal Horticultural Society (London, England) Colour Chart, 2001, except where common terms of color are used.

For a comparison, several physical characteristics of a non-patented *Clematis* variety *Clematis*×*cartmanii* 'Joe' are compared to 'Evipo045' in Chart 1.

CHART 1

| | 'Evipo045' | 'Joe' |
|---|---|---|
| Flower diameter | 40 mm | 35 mm |
| Leaf morphology | Generally palmate | Digitate |
| Tepal overlap | none | partial |

FLOWER AND FLOWER BUD

Blooming habit: Very early flowering. Recurrent. The natural flowering period is from early April to September.

Flower bud:

*Size*.—Normally 15 mm in length. Bud diameter is 6 mm.

*Bud form*.—Tubular.

*Coloration*.—White Group 155A.

Peduncle:
*Surface texture*.—Smooth.
*Length*.—On average 40 mm.
*Color*.—Yellow-Green Group 144B.
*Strength*.—Moderately strong.
*Diameter*.—1.5 mm.
Receptacle:
*Surface textire*.—Smooth.
*Shape*.—Funnel.
*Size*.—1 mm (h)×3 mm (w).
*Color*.—Yellow-Green Group 144B.
Flower arrangement:
*Location on vine*.—Old growth in a profusion of panicles.
*Borne*.—Normally in clusters of 3 to 5 flowers per panicle.
Flower bloom:
*Size*.—On average, flowers are 40 mm in diameter and 6 mm in depth.
*Fragrance*.—None.
*Lasting quality*.—Flowers normally remain 7 days on the plant.
Tepals:
*Tepal color*.—The upper surface is White Group 155A with intonations of Yellow Group 11 D toward the flower center. The lower surface is White Group 155A.
*Quantity*.—Normally 6 tepals.
*Size*.—20 mm in length by 11 mm wide.
*Shape*.—Individual tepal elliptic. The tepal apex is somewhat rounded with a small point. The tepal base is acute.
*Apex recurvature*.—None.
*Tepal cross section*.—Flat.
*Margins*.—Entire. No undulations of margin observed.
*Persistence*.—Tepals drop off cleanly.
Reproductive organs:
*Arrangement*.—Open.
*Pollen*.—None observed.
*Anthers*.—Size: 1.5 mm in length. Color: Greyed-Yellow Group 161B. Quantity: On average, 45.
*Filaments*.—Color: White Group 155A. Length: 6 mm.
*Pistils*.—Quantity: On average, 15.
*Stigmas*.—Inferior in location relative to the length of the filaments and the height of the anthers.
*Styles*.—Color: White Group 155A. Length: 5 mm.
Seed head characteristics: None observed.

PLANT

Plant form: Climbing.
Plant growth: Moderately vigorous.
Size: Seasons growth attains 50 cm height. Average spread is 50 cm.

Stems:
*Color*.—Juvenile stems are Yellow-Green Group 144B. Mature stems are Green Group 137C.
*Internodes*.—On average, 25 mm between nodes.
*Length*.—Normally 15 cm from the base of the plant to the flowering portion of the stem.
*Diameter*.—3 mm.
*Texture*.—Mature stems are generally smooth.
Plant foliage:
*Leaf characteristics*.—Evergreen.
*Arrangement*.—Triternate.
*Leaf size*.—Compound leaves are normally 40-45 mm (l)×40-45 mm (w). Leaflets are normally 30 mm (l)× 30 mm (w).
*Abundance*.—4 to 5 leaves per 10 cm of stem.
*Leaf color*.—Green Group 139A on the upper surface. Green Group 138A on lower surface.
*Stipules*.—Absent.
*Petioles*.—Size: 13 mm in length by 1 mm diameter. Texture: Smooth. Color: Yellow-Green Group 146A.
*Petioloule*.—Size: Normally 3 to 5 mm in length by 1 mm diameter. Texture: Smooth. Color: Yellow-Green Group 146A.
*Leaflet shape*.—Generally palmate.
*Margin*.—Deeply incised. Bi-lobed and tri-lobed.
*Surface*.—The upper side is smooth. The lower side is smooth.
*Thickness*.—Moderate.
*Glossiness*.—Glossy.
Disease resistance: Subject to any disease that normally attacks the species. However the variety is more tolerant to *Clematis* wilt than some *Clematis* known to the inventors.
Cold hardiness: The variety is tolerant to USDA Hardiness Zone 6.
Heat tolerance: The variety has been found to be suitable for climate conditions found in the American Horticulture Society heat zone 7.

We claim:

1. A new and distinct variety of *Clematis* plant named 'Evipo045', substantially as described and illustrated, due to its abundant white flowers, attractive long lasting foliage, compact growth, suitability for production from softwood cuttings in pots, and flowering under glasshouse conditions, which make the variety suitable for distribution in the floral industry.

* * * * *